United States Patent [19]

Howard et al.

[11] Patent Number: 5,419,202

[45] Date of Patent: May 30, 1995

[54] PAPERBOARD SCORE BEND TESTING DEVICE AND METHOD

[75] Inventors: George M. Howard, West Chester; Thomas W. Rogers, Norristown, both of Pa.; Joseph M. McCullin, Wilmington, Del.

[73] Assignee: Jefferson Smurfit Corporation, Clayton, Mo.

[21] Appl. No.: 219,073

[22] Filed: Mar. 28, 1994

[51] Int. Cl.6 ............................................. G01N 3/20
[52] U.S. Cl. ........................................ 73/849; 493/37
[58] Field of Search ................... 73/850, 851, 862.451, 73/862.452, 862.453, 862.454, 862.46, 854, 849, 857, 788, 774, 794; 493/37, 162, 166, 167, 176

[56] References Cited

U.S. PATENT DOCUMENTS

| | | | |
|---|---|---|---|
| 2,479,303 | 8/1949 | Boor et al. | 73/849 |
| 3,176,510 | 4/1965 | Kimmell et al. | 73/862.454 |
| 3,178,936 | 4/1965 | Finsterwalder | 73/854 |
| 4,046,001 | 9/1977 | Maeda et al. | 73/774 |
| 4,358,962 | 11/1982 | Ashby et al. | 73/849 |
| 4,474,067 | 10/1984 | Cherry, III et al. | 73/794 |
| 4,480,487 | 11/1984 | Kunzfeld | 73/862.454 |
| 4,753,113 | 6/1988 | Lumsden | 73/849 |
| 5,016,477 | 5/1991 | Crespi | 73/849 |
| 5,218,842 | 6/1993 | Tower, Jr. et al. | 73/794 |

FOREIGN PATENT DOCUMENTS 59-56134  3/1984  Japan .......................... 73/862.454

Primary Examiner—Richard E. Chilcot, Jr.
Assistant Examiner—James M. Olsen
Attorney, Agent, or Firm—Richard W. Carpenter

[57] ABSTRACT

A device and method for measuring the force or pressure required to break a score and bend a sheet of paperboard along a pre-formed score line. The device includes means for clamping one portion of the sheet between a pair of stationary plates, with another portion of the sheet extending beyond the plates, and a moveable plate co-planar with, but spaced a short distance from, one of the stationary plates and engageable with the other portion of the sheet. The device includes a mechanism for moving the moveable plate out of the plane of one of the stationary plates, to break the score and bend the sheet at the score line, and a gauge for measuring the force required to bend the paperboard sheet at the score line.

15 Claims, 1 Drawing Sheet

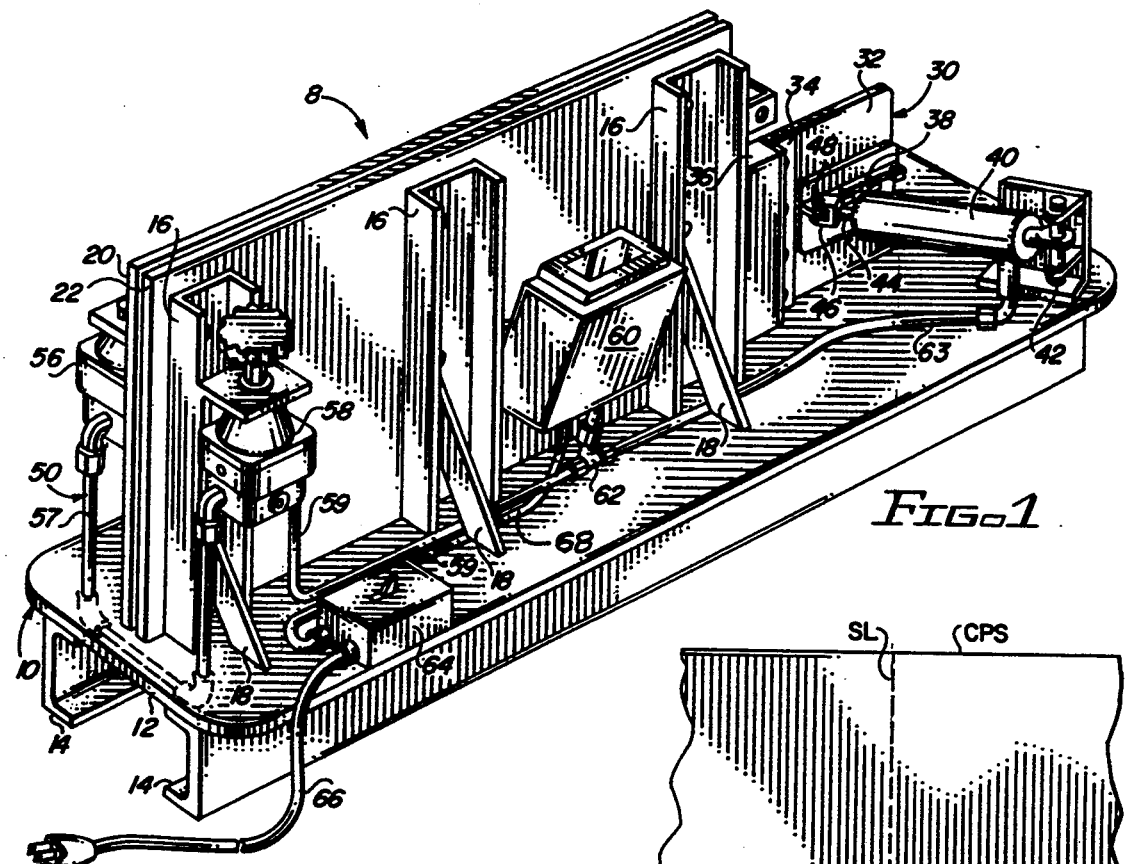
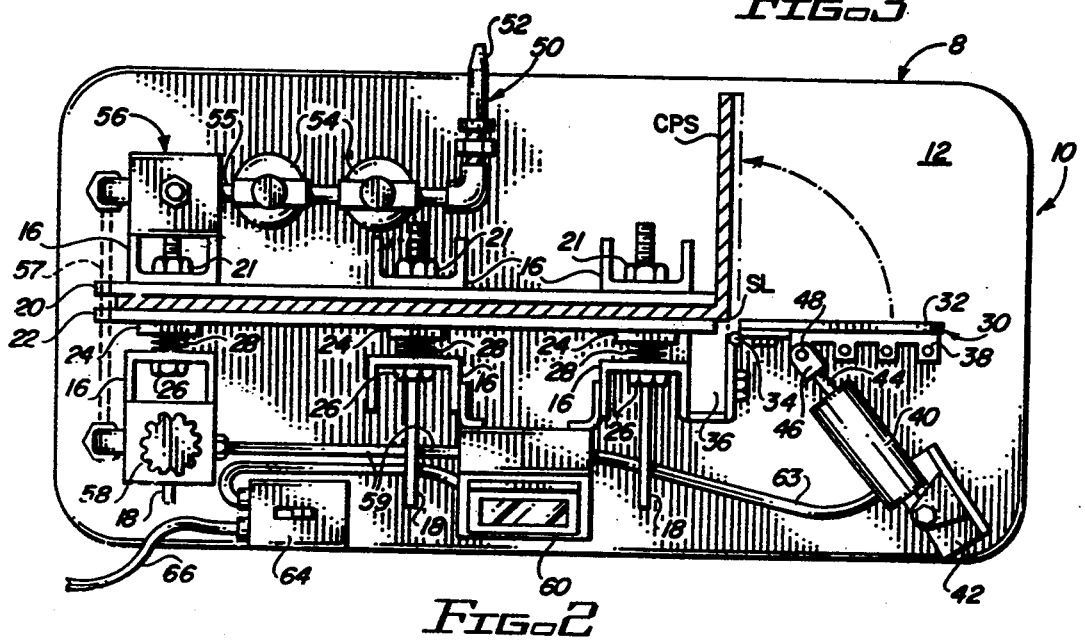

PAPERBOARD SCORE BEND TESTING DEVICE AND METHOD

BACKGROUND OF THE INVENTION

1. Field of the Invention

This invention relates to testing devices, and more particularly to a device for measuring the force or pressure required to break a score and bend a sheet of corrugated paperboard along a pre-formed score line in the sheet.

2. Description of the Background Art

A background art search directed to the subject matter of this invention conducted in the United States Patent and Trademark Office disclosed the following U.S. Pat. Nos.:

4,046,001 4,358,962 4,474,067 4,753,113 5,016,477.

None of the patents uncovered in the search discloses a device or method for measuring the force or pressure required to break a score and bend a sheet of corrugated paperboard along a pre-formed score line in the sheet, which device comprises means for clamping a portion of the sheet between a pair of stationary plates, with another portion of the sheet extending beyond the plates; a third plate co-planar with, but spaced a short distance from, one of the stationary plates and engageable with the other portion of the sheet; means for moving the third plate out of the plane of one of the stationary plates; and means for measuring the force required to break the score and bend the paperboard sheet at the score line.

SUMMARY OF THE INVENTION

It is a primary object of the invention to provide a device and method for measuring the force required to break a score and bend a pre-scored sheet of paperboard at the score line.

A more specific object of the invention is the provision of a device including means to clamp a portion of a pre-scored paperboard sheet between a pair of stationary plates, with another portion of the sheet extending beyond the plates; means to move a moveable plate, engageable with the other portion of the sheet, out of the plane of one of said stationary plates to break the score and bend said sheet at the score line; and means for measuring the force required to bend said paperboard sheet at said score line.

These and other objects of the invention will be apparent from an examination of the following description and drawings.

BRIEF DESCRIPTION OF THE DRAWINGS

FIG. 1 is a fragmentary isometric view of a paperboard score bend testing device embodying features of the invention;

FIG. 2 is a top plan view of the structure illustrated in FIG. 1, shown with a paperboard sheet in the device after it has been folded; and FIG. 3 is a reduced scale plan view of a portion of the paperboard sheet illustrated in the other views.

It will be understood that, for purposes of clarity, certain elements may have been omitted from certain views intentionally, where they are believed to be illustrated to better advantage in other views.

DESCRIPTION OF THE PREFERRED EMBODIMENT

Containers and other articles formed of paperboard commonly have certain areas creased or scored, when the articles are made, to facilitate their being folded into erected condition.

Manufacturers who package their products in corrugated or other types of paperboard containers are concerned with the force required to break the scores and bend the container flaps when the containers are erected or closed, whether the containers are erected by machine or manually. Therefore, many manufacturers, when they establish specifications for their packaging, include specific details regarding the force required to break the scores and bend the paperboard along the score lines. In the case of thicker or heavier sheets of paperboard, such as corrugated paperboard, this is especially important to manufacturers.

In view of this, it is especially important for the makers of the paperboard products to be able to comply with these requirements. In the past much of the so-called testing of the force required to bend paperboard scores has been on a trial and error basis.

The present invention provides for a scientific means for measuring the force required to break scores and bend paperboard.

Referring now to the drawings for a better understanding of the invention, it will be seen that the device, indicated generally at 8 in FIGS. 1 and 2, is used to measure the force required to bend a sheet of corrugated paperboard CPS along a pre-formed score line, indicated at SL in FIG. 3.

The device 8 comprises a base 10 that includes a relatively thin, flat, preferably rectangular, metal plate 12 mounted on and supported by a pair of horizontally extending support beams 14, each comprising a channel bar.

Two rows of vertically extending support columns 16 facing each other are positioned on the base plate 12. Each support column 16 comprises a channel bar, secured at its lower end, as by welding, to base plate 12. Each column 16 may be reinforced by a brace or strut 18, extending diagonally down from the column to the base plate and secured to both the column and the base plate, preferably by welding.

The function of the support columns of each row is to support a pair of relatively thin, flat, stationary plates 20 and 22, preferably formed of plexiglass, between which plates may be clamped a portion of a paperboard sheet, as hereinafter described.

As best seen in FIG. 2, rear plate 20 is fixedly secured to the front sides of the support columns 16 of the rear row of columns by nuts and bolts indicated at 21; whereas front plate 22 is adjustably secured to the rear sides of the support columns 16 of the front row of columns to allow the plates to be moved to vary the distance between the plates depending on the thickness of the sheet of paperboard to be tested.

This is accomplished by means of spring collars or pads 24 secured to the front surface of plate 22 and which are adjustably connected to the adjacent support columns of the front row by nuts and bolts 26, with coil springs 28 positioned between the columns and the plate 22. If desired, this arrangement can be reversed, with the front plate 22 being fixedly mounted, and the rear plate 20 being adjustably mounted.

The important point is that one portion of a paperboard sheet to be tested must be clamped tightly between the first and second stationary plates with another portion of the sheet extending beyond the ends of the stationary plates, and with the score line of the paperboard positioned at a specific location immediately beyond the plate ends.

The sheet of paperboard can be bent at the score line by a paperboard bending assembly, indicated generally at 30, which includes a third relatively thin, flat, preferably plexiglass, movable plate 32, that is co-planar with, but spaced a slight distance from, front stationary plate 22.

Plate 32 is arranged and disposed to engage the other portion of the paperboard sheet, that extends beyond the ends of the stationary plates, and is mounted for pivotal movement into and out of the plane of the front stationary plate 22.

The pivotal mounting includes a hinge 34 having one side connected to a hinge block 36, that is secured to an adjacent support column 16, and another side connected to a bracket 38, that is secured to the front side of moveable plate 32.

Movement of plate 32 is accomplished by a pneumatic cylinder 40 connected to a mounting bracket 42 on the base plate 12. Cylinder 40 includes a piston 44, which is connected by a clevis 46 and pin 48 to movable plate bracket 38.

The cylinder piston is actuated by air pressure which is delivered, regulated, and measured by an air control system indicated generally at 50 and best illustrated in FIG. 2.

Air under pressure enters the system through intake line 52 where it passes to one or more air filters 54 and then through line 55 to an air pressure regulator 56, where the incoming air pressure can be adjusted to an approximate figure. From the air pressure regulator the air passes through line 57 to a precision air regulator 58, where the pressure can be controlled more accurately, as described later herein.

From the precision air regulator the air passes through line 59 to an air pressure gauge 60, preferably with a digital readout display. The air enters the air pressure gauge 60 through one element of a T-fitting 62; the other element of the fitting is connected to an air line 63 which carries the air to cylinder 40.

The system also includes an electrical power on/off switch 64, mounted on base plate 12 and connected to a 115 volt power source, by a line 66, and to the air pressure gauge 60, by a line 68.

In order to operate the device to determine the force required to break a score and bend a paperboard sheet along a score line, the first step is to clamp one portion of the sheet snugly between the stationary plates 20 and 22, with another portion of the sheet extending outwardly beyond the ends of the plates and lying against the rear surface of moveable plate 32, and with the score line SL located between the ends of plates 20 and 22 and the related end of movable plate 32, as seen in FIG. 2.

After the paperboard sheet has been clamped in place the electrical switch 64 is turned on, and the digital readout will be displayed. Air pressure regulator 56 should be in a closed position at this time, so no air can come through to the cylinder 40.

The air pressure regulator 56 is then opened and set to a predetermined pressure that is greater that the pressure expected to be required to bend the paperboard sheet.

The precision air regulator 58 is then slowly and carefully adjusted to increase the air pressure in both the air pressure gauge 60 and the air cylinder 40, until the moveable plate 32 moves the other portion of the paperboard sheet to break the score and bend the sheet at the score line. When this occurs, the digital readout on the air pressure gauge will indicate the amount of force required to break the score and bend the sheet.

It should be understood that, while the invention has been described as including a pneumatic air cylinder, if desired, a hydraulic cylinder may be used to move the moveable plate.

Thus, it will be appreciated that the invention provides a relatively simple, yet scientifically accurate, device and method for measuring the force required to break a score and bend a paperboard sheet at a preformed score line, regardless of the weight and/or thickness of the paperboard.

What is claimed is:

1. A device for measuring the force required to break a score and bend a sheet of paperboard along a preformed score line in said sheet, said device comprising:
   (a) a horizontally disposed base;
   (b) two parallel rows of stationary, vertical columns secured to said base and extending upwardly therefrom adjacent each other;
   (c) a pair of relatively, thin, flat, parallel, vertically extending, non-pivotal, first and second plates secured to adjacent faces of respective of said columns;
   (d) means for moving said second plate a relatively short distance toward and away from said first plate to clamp, between said plates, one portion of a paperboard sheet, with another portion of said sheet extending outwardly beyond corresponding end edges of said plates and having therein a preformed score line located immediately outwardly adjacent and parallel to said corresponding plate end edges;
   (e) a flat, vertically extending, pivotal third plate positioned on said base adjacent and co-planar with said first non-pivotal plate for engagement with said other paperboard portion and mounted for movement about a vertical axis located immediately outwardly adjacent and parallel to said corresponding plate end edges;
   (f) a pneumatic cylinder having a piston engageable with said pivotal plate and operable to move it out of the plane of said first stationary plate to bend said paperboard sheet along said score line;
   (g) means for delivering air under accurately controlled pressure to said cylinder;
   (h) means for measuring the air pressure required to move said pivotal plate the distance required to break said score and bend said sheet at said score line.

2. A device according to claim 1, wherein said means for delivering air under pressure to said cylinder includes at least one precision air regulator that allows an operator to control accurately the pressure of the air being delivered.

3. A device according to claim 1, wherein said force measuring means includes an air pressure gauge interposed between a precision air regulator and said pneumatic cylinder.

4. A device for measuring the force required to break a score and bend a sheet of paperboard along a preformed score line in said sheet, comprising:
   (a) a horizontally disposed base;
   (b) two parallel rows of stationary, vertical columns secured to said base and extending upwardly therefrom adjacent each other;
   (c) a pair of relatively, thin, flat, parallel, vertically extending, non-pivotal, first and second plates secured to adjacent faces of respective of said columns;
   (d) means for moving said second plate a relatively short distance toward and away from said first plate to clamp, between said plates, one portion of a paperboard sheet, with another portion of said sheet extending outwardly beyond corresponding end edges of said plates and having therein a preformed score line located immediately outwardly adjacent and parallel to said corresponding plate end edges;
   (e) a flat, vertically extending, pivotal third plate positioned on said base adjacent and co-planar with said first non-pivotal plate for engagement with said other paperboard portion and mounted for movement about a vertical axis located immediately outwardly adjacent and parallel to said corresponding plate end edges;
   (f) moving means engageable with and operable to move said paperboard sheet other portion out of the plane of said one portion to bend said paperboard along said score line;
   (g) fluid pressure means engageable with and operable to actuate said moving means;
   (h) measuring means for measuring the amount of force required to move said paperboard sheet other portion the distance required to break said score and bend said sheet at said score line.

5. A device according to claim 4, wherein said moving means includes a pneumatic cylinder having a piston engageable with said moveable plate and operable to move it out of the plane of said one stationary plate.

6. A device according to claim 5, and including means for delivering air under a controlled pressure to said pneumatic cylinder.

7. A device according to claim 6, wherein means for delivering air under a controlled pressure includes an air pressure regulator.

8. A device according to claim 7, wherein said force measuring means includes an air pressure gauge interposed between said pressure air regulator and said pneumatic cylinder.

9. A device for measuring the force required to break a score and bend a sheet of paperboard along a preformed score line in said sheet, comprising:
   (a) a horizontally disposed base;
   (b) two parallel rows of stationary, vertical columns secured to said base and extending upwardly therefrom adjacent each other;
   (c) a pair of relatively, thin, flat, parallel, vertically extending, non-pivotal, first and second plates secured to adjacent faces of respective of said columns;
   (d) means for moving said second plate a relatively short distance toward and away from said first plate to clamp, between said plates, one portion of a paperboard sheet, with another portion of said sheet extending outwardly beyond corresponding end edges of said plates and having therein a preformed score line located immediately outwardly adjacent and parallel to said corresponding plate end edges;
   (e) a flat, vertically extending, pivotal third plate positioned on said base adjacent and co-planar with said first non-pivotal plate for engagement with said other paperboard portion and mounted for movement about a vertical axis located immediately outwardly adjacent and parallel to said corresponding plate end edges;
   (f) moving means engageable with and operable to move said paperboard sheet other portion out of the plane of said one portion to bend said paperboard along said score line;
   (g) measuring means for measuring the amount of force required to more said paperboard sheet other portion the distance required to break said score and bend sheet at said score line.

10. A device according to claim 9, wherein said moving means includes a moveable flat plate disposed mounted for pivotal movement about an axis parallel to the score line of said paperboard sheet.

11. A device according to claim 9, and including a fluid pressure means comprised of a fluid pressure cylinder and a moveable piston engageable with said moving means.

12. A device according to claim 11, and including means for delivering fluid under a controlled pressure to said cylinder.

13. A device according to claim 12, wherein means for delivering fluid under a controlled pressure includes an air pressure regulator.

14. A device according to claim 9, wherein said measuring means includes a fluid pressure gauge connected to said fluid pressure means.

15. A device according to claim 9, wherein said fluid pressure means includes a fluid pressure regulator that allows an operator to deliver fluid at a precise amount of pressure to said cylinder.

* * * * *